United States Patent
Shen

(10) Patent No.: US 10,661,100 B2
(45) Date of Patent: May 26, 2020

(54) METHOD FOR MEASURING FIELD SIZE FACTOR FOR RADIATION TREATMENT PLANNING USING PROTON PENCIL BEAM SCANNING

(71) Applicant: MAYO FOUNDATION FOR MEDICAL EDUCATION AND RESEARCH, Rochester, MN (US)

(72) Inventor: Jiajian Shen, Scottsdale, AZ (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 260 days.

(21) Appl. No.: 15/914,707

(22) Filed: Mar. 7, 2018

(65) Prior Publication Data

US 2018/0256919 A1    Sep. 13, 2018

Related U.S. Application Data

(60) Provisional application No. 62/468,637, filed on Mar. 8, 2017.

(51) Int. Cl.
*A61N 5/10* (2006.01)

(52) U.S. Cl.
CPC .......... *A61N 5/1043* (2013.01); *A61N 5/1075* (2013.01); *A61N 5/1044* (2013.01);
(Continued)

(58) Field of Classification Search
CPC .... A61N 2005/1074; A61N 2005/1087; A61N 5/1043; A61N 5/1044; A61N 5/1075; A61N 5/1081
See application file for complete search history.

(56) References Cited

U.S. PATENT DOCUMENTS

| | | | |
|---|---|---|---|
| 7,378,672 B2 * | 5/2008 | Harada | A61N 5/10 250/359.1 |
| 8,263,954 B2 | 9/2012 | Iwata | |

(Continued)

OTHER PUBLICATIONS

Anferov, V.A. "Scan pattern optimization for uniform proton beam scanning." Medical physics 36.8 (2009): 3560-3567.
(Continued)

*Primary Examiner* — Wyatt A Stoffa
(74) *Attorney, Agent, or Firm* — Quarles & Brady LLP

(57) ABSTRACT

Systems and methods for radiation treatment planning in proton therapy using pencil beam scanning ("PBS") are described. More particularly, the systems and methods described in the present disclosure related to quantifying the output from a proton therapy system implementing PBS. The systems and methods described in the present disclosure can therefore be implemented when commissioning a new proton therapy system, or when performing quality assurance ("QA") on a proton therapy system. A spot delivery pattern that includes a spiral out pattern is used for beam delivery. A number of control points along the spot delivery pattern define a beam pause time during which delivery of the proton beam is paused. Radiation measurements are obtained at the control points and at the end of the spot delivery pattern, and these radiation measurements are used to compute field size factors for field sized associated with the segments of the spot delivery pattern.

19 Claims, 4 Drawing Sheets

(52) U.S. Cl.
CPC .... *A61N 5/1081* (2013.01); *A61N 2005/1074* (2013.01); *A61N 2005/1087* (2013.01)

(56) References Cited

U.S. PATENT DOCUMENTS

| | | | | |
|---|---|---|---|---|
| 8,294,127 | B2* | 10/2012 | Tachibana | A61N 5/1043 250/310 |
| 9,596,746 | B2* | 3/2017 | Tsubuku | A61N 5/1068 |
| 2011/0108737 | A1* | 5/2011 | Pu | A61N 5/10 250/398 |
| 2012/0228521 | A1* | 9/2012 | Honda | A61N 5/1043 250/492.3 |
| 2012/0264998 | A1* | 10/2012 | Fujitaka | A61N 5/1036 600/1 |
| 2012/0305790 | A1* | 12/2012 | Hanawa | A61N 5/1043 250/393 |
| 2015/0087887 | A1* | 3/2015 | Iwata | A61N 5/103 600/1 |
| 2015/0099917 | A1* | 4/2015 | Bula | A61N 5/1044 600/1 |
| 2015/0126798 | A1* | 5/2015 | Iwata | A61N 5/1043 600/1 |
| 2018/0326224 | A1* | 11/2018 | Umezawa | A61N 5/1043 |
| 2019/0091488 | A1* | 3/2019 | Ding | A61N 5/103 |

OTHER PUBLICATIONS

Both S, et al. Development and clinical implementation of a universal bolus to maintain spot size during delivery of base of skull pencil beam scanning proton therapy. Int J Radiat Oncol Biol Phys. 2014;90(1):79-84.

Frank SJ, et al. Multifield Optimization Intensity Modulated Proton Therapy for Head and Neck Tumors: A Translation to Practice. Int J Radiat Oncol Biol Phys. 2014;89(4):846-53.

Lewis D, et al. An efficient protocol for radiochromic film dosimetry combining calibration and measurement in a single scan. Med Phys. 2012;39(10):6339-50.

Li Y, et al. Beyond Gaussians: a study of single-spot modeling for scanning proton dose calculation. Phys Med Biol. 2012;57(4):983-97.

Lin L, et al. Experimental characterization of two-dimensional spot profiles for two proton pencil beam scanning nozzles. Phys Med Biol. 2014;59(2):493-504.

Lin LY, et al. A novel technique for measuring the low-dose envelope of pencil-beam scanning spot profiles. Phys Med Biol. 2013;58(12):N171-80.

Lin LY, et al. Use of a novel two-dimensional ionization chamber array for pencil beam scanning proton therapy beam quality assurance. J Appl Clin Med Phys. 2015;16(3):270-6.

Lomax AJ, et al. Treatment planning and verification of proton therapy using spot scanning: initial experiences. Med Phys. 2004;31(11):3150-7.

Pedroni E, et al. Experimental characterization and physical modelling of the dose distribution of scanned proton pencil beams. Phys Med Biol. 2005;50(3):541-61.

Sawakuchi GO, et al. Experimental characterization of the low-dose envelope of spot scanning proton beams. Phys Med Biol. 2010;55(12):3467-78.

Schaffner B. Proton dose calculation based on in-air fluence measurements. Phys Med Biol. 2008;53(6):1545-62.

Shen J, et al. An efficient method to determine double Gaussian fluence parameters in the Eclipse proton pencil beam model. Med Phys. 2016;43(12):6544-51.

Shen J, et al. Impact of range shifter material on proton pencil beam spot characteristics. Med Phys. 2015;42(3):1335.

Shen, J. et al. "Using field size factors to characterize the in-air fluence of a proton machine with a range shifter." Radiation Oncology 12.1 (2017): 52.

Zhu XR, et al. Commissioning dose computation models for spot scanning proton beams in water for a commercially available treatment planning system. Med Phys. 2013;40(4):041723.

\* cited by examiner

METHOD FOR MEASURING FIELD SIZE
FACTOR FOR RADIATION TREATMENT
PLANNING USING PROTON PENCIL BEAM
SCANNING

CROSS-REFERENCE TO RELATED
APPLICATIONS

This application claims the benefit of U.S. Provisional Patent Application Ser. No. 62/468,637, filed on Mar. 8, 2017, and entitled "Efficient Method to Measure the Field Size Factor or Out Put Factor for Proton Pencil Beam Scanning."

BACKGROUND

Pencil beam scanning ("PBS") techniques have gained more popularity in proton therapy centers because PBS has reduced neutron dose; no need for apertures and compensators; and intrinsically enables intensity modulated proton therapy ("IMPT"). Due to technical challenges, current clinical PBS systems cannot provide protons with energies below 70 MeV. This limits the ability to treat shallow tumors (e.g., tumors at a depth less than 4 cm) unless a range shifter ("RS") is added at the end of the nozzle.

The spot sizes of proton beamlets increase when a RS is used, and these increases in spot size are more pronounced for low proton energies. This increase in spot size is due to the scattering of protons from the RS and the large air gap between the RS and isocenter. Additionally, the RS creates low-signal tails in the beam profile due to large-angle multiple Coulomb scattering and nuclear interactions. These low-signal tails can extend laterally more than 10 cm from the spot center. Clinically these low dose tails manifest themselves in an increase of output with field sizes, a phenomenon known as the field size effect. To address this clinically-relevant effect, the treatment planning system ("TPS") can use two Gaussian distributions to model the proton fluence: one for the primary fluence and the second for the tails. The modeling process for a RS in a TPS is further complicated by spot size enlargement and the associated low-dose tails.

The process of commissioning a proton therapy system, or performing routine quality assurance on such a system, can also be time consuming. Currently, field size factors are computed based on radiation measurements obtained by scanning a field-of-view using different beam deliveries. That is, the beam is scanned across the entire field and radiation measurements are recorded before the beam is moved over the next field. It would be beneficial to provide a method for measuring field size factor in multiple different field sizes using a more efficient process.

SUMMARY OF THE DISCLOSURE

The present disclosure addresses the aforementioned drawbacks by providing a method for quantifying an output of a proton therapy system. The method includes generating control instructions for the proton therapy system with a computer system. The control instructions define a spot delivery pattern through which a proton beam is to be moved. The spot delivery pattern includes a plurality of spot delivery pattern segments each corresponding to different field sizes, and a plurality of control points, each control point separating a first and second spot delivery pattern segment selected from the plurality of spot delivery pattern segments and defining a proton beam pause time during which the proton beam is paused. The plurality of spot delivery pattern segments collectively define a spiral pattern that begins at a center of a field-of-view of the proton therapy system and spirals outward to a periphery of the field-of-view. The control instructions are provided to the proton therapy system and the proton therapy system is operated using the control instructions. A radiation measurement is acquired by a radiation detector during each proton beam pause time, each radiation measurement being associated with one of the different field sizes. A plurality of field size factors are computed with the computer system, including a field size factor for each of the different field sizes using the radiation measurements acquired for that different field size. An output of the proton therapy system is then quantified based in part on the plurality of field size factors.

It is another aspect of the present disclosure to provide a method for controlling the operation of a proton therapy system. A proton beam is extracted from a synchrotron and transported from the synchrotron through a nozzle to a radiation detector. The proton beam is scanned over the radiation detector along a spot delivery pattern. The spot delivery pattern includes a plurality of spot delivery pattern segments each corresponding to different field sizes, and a plurality of control points, each control point separating a first and second spot delivery pattern segment selected from the plurality of spot delivery pattern segments and defining a proton beam pause time during which delivery of the proton beam is paused. The plurality of spot delivery pattern segments collectively define a spiral pattern that begins at a center of a field-of-view of the proton therapy system and spirals outward to a periphery of the field-of-view.

It is another aspect of the present disclosure to provide a controller for controlling the operation of a proton therapy system. The controller includes a memory and a processor. The memory has instructions stored thereon that define a spot delivery pattern that includes a plurality of spot delivery pattern segments each corresponding to different field sizes, and a plurality of control points, each control point separating a first and second spot delivery pattern segment selected from the plurality of spot delivery pattern segments and defining a proton beam pause time during which a proton beam is to be paused. The plurality of spot delivery pattern segments collectively define a spiral pattern that begins at a center of a field-of-view and spirals outward to a periphery of the field-of-view. The processor is in communication with the memory and is operable to receive the instructions stored on the memory. When the instructions are implemented on the processor it is caused to control the operation of a proton therapy system to deliver a proton beam along the spot delivery pattern and to measure radiation during each proton beam pause time.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for radiation treatment planning in proton therapy using pencil beam scanning ("PBS"). More particularly, the systems and methods described in the present disclosure related to quantifying the output from a proton therapy system implementing PBS. The systems and methods described in the present disclosure can therefore be implemented when commissioning a new proton therapy system, or when performing quality assurance ("QA") on a proton therapy system.

Using the techniques described in the present disclosure, field size factor ("FSF") is computed for multiple different field sizes, and these FSFs are used to characterize proton fluence values that are used for commissioning a proton therapy system, or for performing QA on a proton therapy system already in use. In general, a spot delivery pattern is designed and implemented in such a way that the proton beamlets are delivered in a pattern during which the beam delivery is paused at a predefined number of control points. At each control point, a proton fluence measurement is acquired, and these dose measurements are used to estimate the FSFs for each different field size. The FSFs can then be used to confirm that the appropriate output is being delivered by the proton therapy system, whether for commissioning the system or for performing QA. For instance, when commissioning the proton therapy system, the FSFs can be used to configure a model for the treatment planning system ("TPS").

Figure 1:
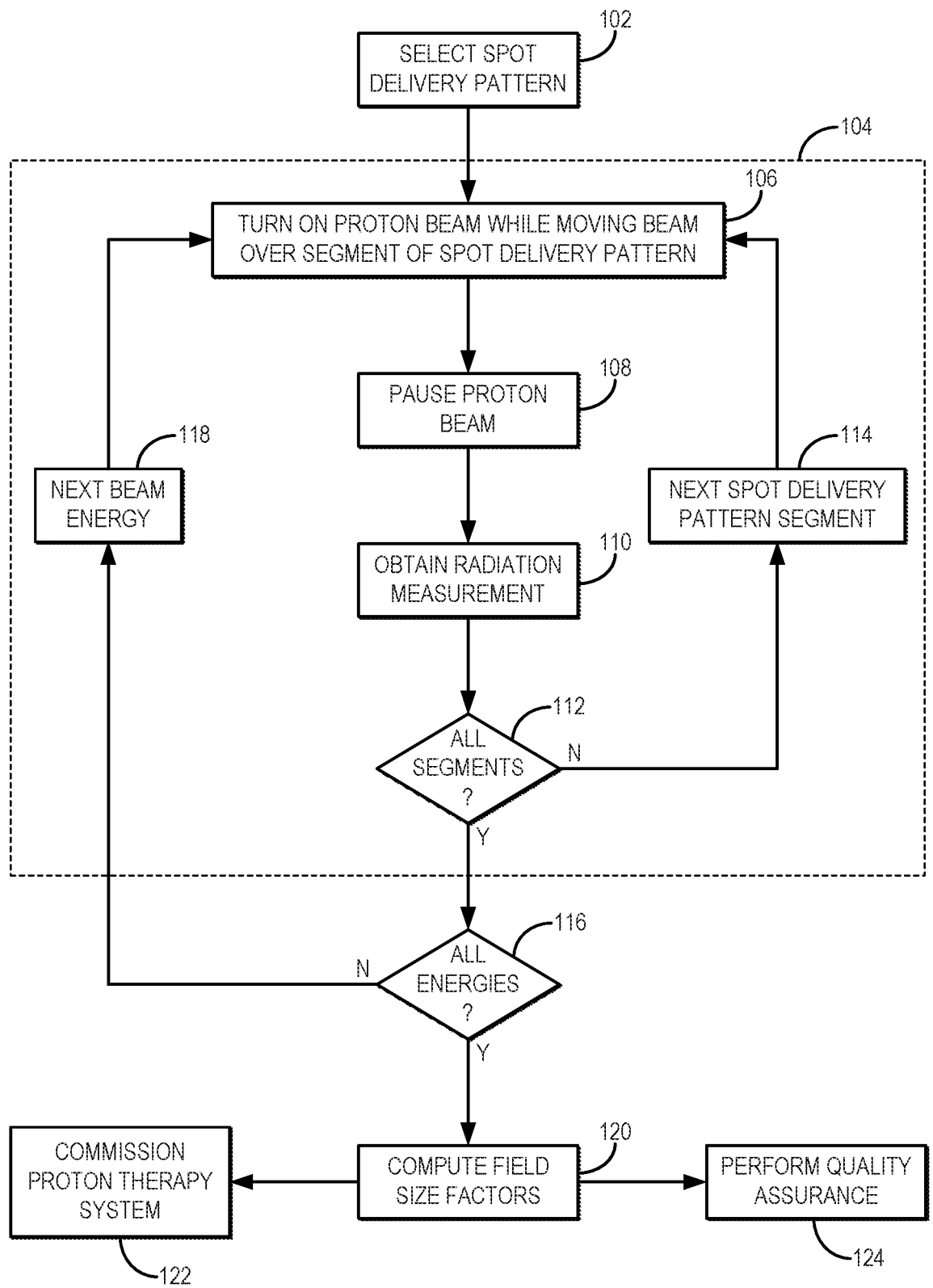
FIG. 1 is a flowchart setting forth the steps of an example method for measuring field size factors in multiple different field sizes during a single proton beam delivery.

Referring now to FIG. 1, a flowchart is illustrated as setting forth the steps of an example method for quantifying the output of a proton therapy system. The method includes designing, or otherwise selecting, a spot delivery pattern, as indicated at step 102. The spot delivery pattern can be included in control instructions that, when provided to a proton therapy system, control the proton beam delivery of the proton therapy system to deliver a proton beam over the prescribed spot delivery pattern.

Figure 2:
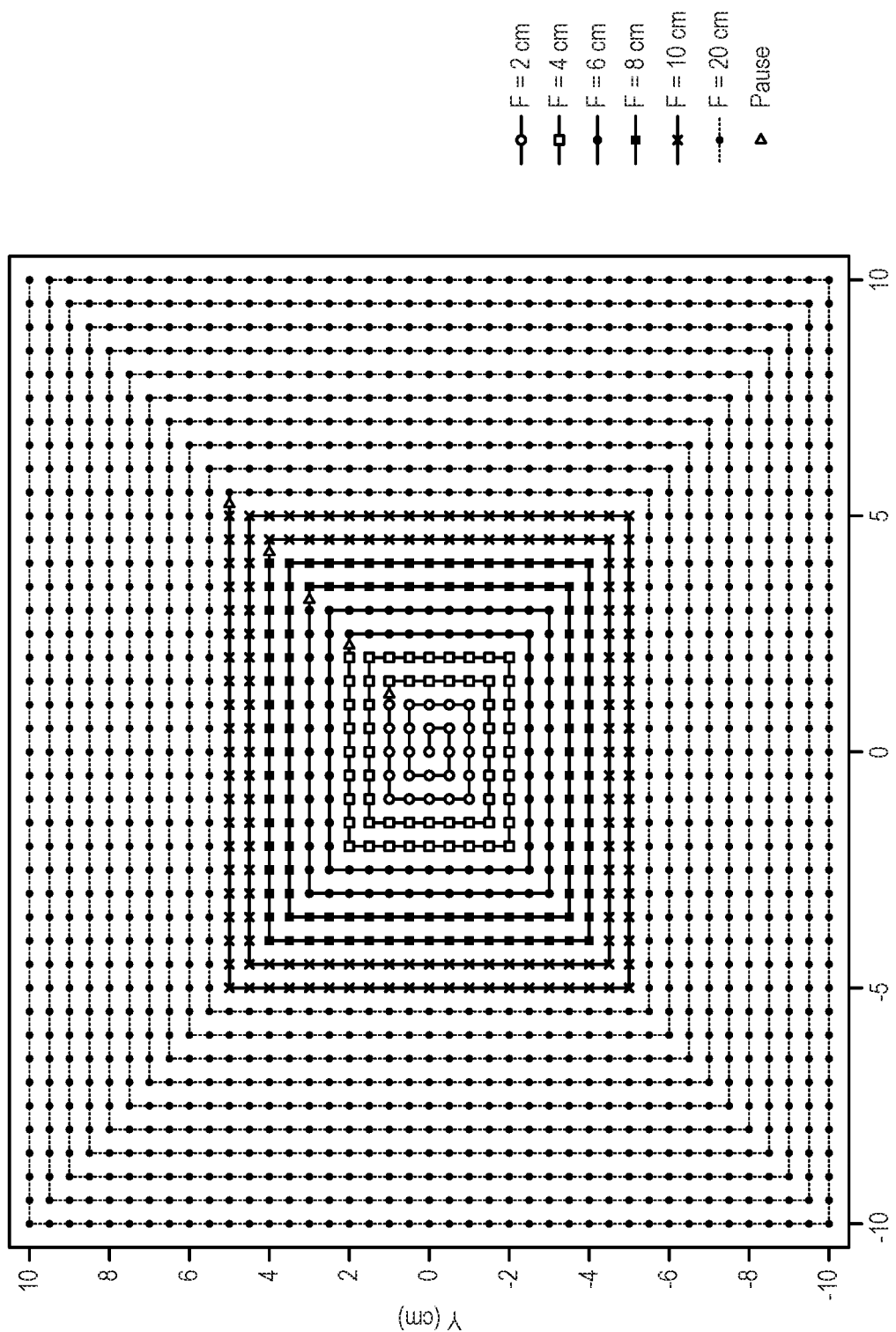
FIG. 2 is an example of a spot delivery pattern that can be implemented with the methods described in the present disclosure.

An example of a spot delivery pattern that can be implemented with the methods described in the present disclosure is shown in FIG. 2. In general, the spot delivery pattern includes a spiral-out path that begins in the center of the field-of-view and spirals outward to the periphery of the field-of-view. The spot delivery pattern is divided into a number of different segments, each corresponding to a different field size. When transitioning from one segment to the next, the beam delivery is paused at which time a radiation measurement is obtained before continuing the beam delivery along the next segment of the spot delivery pattern. The points at which the beam delivery is paused may be referred to as control points.

In the example shown in FIG. 2, the spot delivery pattern includes five control points corresponding to the transitions between six different field sizes (2 cm, 4 cm, 6 cm, 8 cm, 10 cm, and 20 cm). Although FIG. 2 shows segments of the spot delivery pattern corresponding to six different field sizes, the spot delivery pattern can be segmented to any number of desirable field sizes. The fields between 2 cm and 10 cm are sampled more densely than between 10 cm and 20 cm in the example shown in FIG. 2 because there is typically a larger gradient over these smaller field sizes. In other implementations, however, different samplings can be used.

This type of spot delivery pattern described in the present disclosure has several advantageous features. As one advantageous feature, a single spot delivery pattern is used to obtain measurements of proton fluence over multiple different field sizes in a single beam delivery. This is different from traditional approaches, which utilize a different spot delivery pattern that spans the entire field for each different field size. Using the methods described in the present disclosure, a significant gain in efficiency can be realized since shorter beam-on time is required to obtain the measurements necessary for commissioning the proton therapy system, or for performing routine QA. As one non-limiting example, the beam-on time can be reduced by a factor of five or more. Reloading the spot pattern files and waiting for the proton system's various interlocks to clear, as is currently done, takes time, so pausing one beam a number of times represents a significant improvement in efficiency over running separate beams for each different field size.

As another advantageous feature, the beam delivery begins in the center of the field-of-view and moves outward to the periphery of the field-of-view. This is different from more traditional raster scan patterns, which begin beam delivery on one peripheral side of the field-of-view before moving towards the center of the field-of-view and then to the opposite peripheral side of the field-of-view. Advantageously, starting the beam delivery in the center of the field-of-view allows for greater consistency in the beam delivery at the center of the field-of-view, which increases the reliability of the fluence and FSF measurements.

Referring again to FIG. 1, after the spot delivery pattern has been chosen the proton therapy system is operated to deliver a proton beam in accordance with the instructions provided by the selected spot delivery pattern, as generally indicated at process block 104. As noted above, the delivery includes turning on the proton beam and moving the beam over the first segment of the spot delivery pattern to the first control point, as indicated at step 106. Delivering the proton beam may include extracting protons from a cyclotron or synchrotron, transporting the protons from the cyclotron or synchrotron through a nozzle and into a dosimeter, phantom, patient, or other suitable target. The beam is then paused when the control point is reached, as indicated at step 108. While the beam is paused, a radiation measurement is made, as indicated at step 110. As noted above, the radiation measurement made at each control point corresponds to a different field size; hence, the first radiation measurement corresponds to the first field size.

In one example, the radiation measurement can be a proton fluence measurement obtained using an ionization chamber. For instance, an ionization chamber can be used in the commissioning or QA process to measure charges in the ionization chamber resulting from the proton beam delivery. These charge measurements can be related to proton fluence. In some instances, the proton fluence can be an in-air proton fluence measurement. In some other instances, the proton fluence can be an in-water proton fluence. It will be appreciated that the radiation measurement can be different depending on the type of dosimeter used when commissioning or performing QA on the proton therapy system.

A determination is then made at decision block 112 whether radiation measurements have been made for each prescribed field size. Alternatively, the determination can be whether the proton beam has been moved through all of the prescribed segments of the spot delivery pattern and paused at each prescribed control point. If radiation measurements have not been made for each field size, then the proton beam is turned on again and moved through the next segment of the spot delivery pattern, as indicated at step 114. A radiation measurement is then made at the next control point and the process repeated until all of the radiation measurements have been made. After the last segment of the spot delivery pattern, the proton beam is turned off rather than paused.

When all of the radiation measurements have been made, they can be used for computing a field size factor for each of the different field sizes represented by the different segments of the spot delivery pattern, as indicated at step 116. For instance, the radiation measurements obtained at the first control point can be used to compute the FSF for the first field size, the radiation measurements obtained at the second control point can be used to compute the FSF for the second field size, and so on.

A determination is then made at decision block 118 whether radiation measurements have been made in each prescribed field size for the desired number of beam energies. If not, then the next beam energy is selected, as indicated at step 120, and the proton beam is moved over the spot delivery pattern again in process block 104 to obtain radiation measurements for each field size at the next beam energy. The computed FSFs can then be used for commissioning the proton therapy system, or for performing QA on the proton therapy system, as indicated at steps 122 and 124, respectively.

As one example, commissioning the proton therapy system can include using the radiation measurements to configure a dose computation model in the treatment planning system ("TPS"). The dose computation model can be a double-Gaussian model, or other suitable model. An example of a double-Gaussian model is described below.

By way of non-limiting example, dose can be calculated by convolving the proton fluence with the proton dose kernel. The dose at a given point (x, y, z) may therefore be written as, $$D(x, y, z) = \sum_{E_k} \sum_{Kernel_j} \phi_{E_k}(x, y, z; x_j, y_j, z_j) D_{E_k}^{Kernel}(x - x_j, y - y_j, d(z)); \quad (1)$$

where $\emptyset_{E_k}(x,y,z,x_j,y_j,z)$ is the proton fluence at position (x,y,z) caused by the $j^{th}$ spot, which is centered at $(x_j,y_j)$ and has energy $E_k$; $D_{F_k}^{Kernel}(x-x_j,y-y_j,d(z))$ is the dose kernel; d is the depth in medium; and z is the distance from isocenter along the beam direction. For a double-Gaussian fluence model, the distribution of protons can be described as, $$\phi_{E_k}(x, y, z; x_j, y_j, z) = \Phi_{E_k}^j(z) \left( \frac{1-w_2(E_k)}{2\pi\sigma_1^2(E_k, z)} \exp\left(-\frac{(x-x_j)^2+(y-y_j)^2}{2\sigma_1^2(E_k, z)}\right) + \frac{w_2(E_k)}{2\pi\sigma_2^2(E_k, z)} \exp\left(-\frac{(x-x_j)^2+(y-y_j)^2}{2\sigma_2^2(E_k, z)}\right) \right); \quad (2)$$

where $\Phi_{E_k}^j(z)$ is the maximum fluence of the $j^{th}$ spot, $w_2$ ($E_k$) is the weight of the second Gaussian function, and $\sigma_1(E_k,z)$ and $\sigma_2$ ($E_k,z$) are the standard deviations of the first and second Gaussian, respectively. Properly configuring this double-Gaussian proton fluence model therefore includes finding the optimal, or otherwise appropriate, values of $\sigma_1(E_k,z)$, $\sigma_2(E_k,z)$, and $w_2(E_k)$.

An example of the proton fluence distribution for a single spot is given in Eqn. (2). The FSF for a given field size can be computed by integrating the fluence distributions from all spots inside that field. The proton fluence ("PF") at the center of the field for a given field size ("FS") and spot spacing ("SS") may be described as, $$PF(FS, SS) = \sum_{i=-N}^{N} \sum_{j=-N}^{N} \phi_{spot}\left(r_{ij} = \sqrt{(i \times SS'_x)^2 + (j \times SS'_y)^2}\right) \quad (3);$$

where, $$N = \frac{0.5 \times FS}{SS},$$

$$SS'_x = SS \times \frac{SSD + d}{VSAD_x}, \text{ and}$$

$$SS'_y = SS \times \frac{SSD + d}{VSAD_y}.$$

The parameters $VSAD_x$ and $VSAD_y$ are the virtual SAD in the x-direction and the y-direction, respectively, and $SS'_x$ and $SS'_y$ are the projected spot spacing in the non-isocentric plane in the x-direction and the y-direction, respectively. After calculating the proton fluence for each field size, the FSFs can be obtained by normalizing to a selected field size, which may be 10 cm field size or other suitable field size, $$FSF = \frac{PF(FS)}{PF(FS = 10 \text{ cm})}. \quad (4)$$

A large set of potential Gaussian fit parameters (e.g., $\sigma_1(E_k,z)$, $\sigma_2(E_k,z)$, $w_2(E_k)$) can be used to calculate FSFs for each energy at all positions. The many calculated FSFs can then be compared with the measured FSFs, and the optimal fit parameters chosen to be those that lead to the minimum differences between the measured and calculated FSFs.

With range shifting, a proton beam therapy delivery system can have a varied number of energy layers. In one example system used when implementing the methods described in the present disclosure, a total of 68 energy layers between 80.3 MeV and 175.6 MeV were attainable. The optimal Gaussian fit parameters can be chosen based on the energies that are measured, and the proton fluence parameters for the remaining, non-measured energies can be interpolated based on these optimal fit parameters. All these fluence parameters can then be input into the TPS as part of the beam configuration process.

In an example study, FSFs were measured using the methods described in the present disclosure. In this example study, single-energy spot arrays with a uniform spot spacing of 5 mm and a 20 cm square field size were generated for ten proton energies, ranging from 80.3 MeV to 175.9 MeV. The spot delivery pattern was designed in such a way that the proton beamlets were delivered in a spiral pattern, beginning at the center and proceeding outward. Five control points were also added between selected field sizes to create brief pauses in the beam delivery. The purpose of control points is usually to pause the delivery while the system switches from one proton energy to the next, an automatic process in some proton therapy systems, which can take approximately two seconds. In accordance with the methods described in the present disclosure, however, the control points were used to provide time to manually pause the beam and record the charge collected by the ionization chamber before resuming delivery. The five control points were chosen so that the beam was paused after delivering field sizes of 2 cm, 4 cm, 6 cm, 8 cm, and 10 cm, as shown in the example spot delivery pattern illustrated in FIG. 2. This allowed charge readings to be recorded for six field sizes (including the full 20 cm field) in around three minutes using a single beam delivery. Reloading the spot pattern files and waiting for the proton system's various interlocks to clear takes time, so pausing one beam five times represents a significant improvement in efficiency over running six separate beams for six different field sizes.

In-air charge measurements were made at five positions along the beam direction (in the isocenter plane, ±10 cm and ±20 cm from isocenter) for ten proton energies ranging from 80.3 MeV to 175.9 MeV using six field sizes (2, 4, 6, 8, 10, and 20 cm). The measurements were made with a 34045 Advanced Markus ion chamber (PTW, Freiburg, Germany), which has an effective volume of 0.02 $cm^3$, radius 2.5 mm, and a 1.06 mm WET entrance window.

To keep the chamber in place, it was inserted into a cutout within a 30 cm×30 cm×3 cm acrylic plate machined to hold the chamber. The chamber surface and the effective measurement point (1 mm below the surface) were aligned with the laser, and the couch was moved vertically to bring the chamber to the five measurement positions. At each new couch position, the beam with the smallest field size (2 cm) was delivered five times at the center and at offsets by ±1 mm in the x and y directions from the center, which ensured that the chamber was properly centered before beginning the FSF measurements.

The smallest field size (2 cm) was delivered five times and charges were collected with beam offsets from the current center by ±1 mm in the x and y directions, respectively. The reproducibility of the FSF measurements was checked by repeating them multiple times on multiple days.

Figure 3:
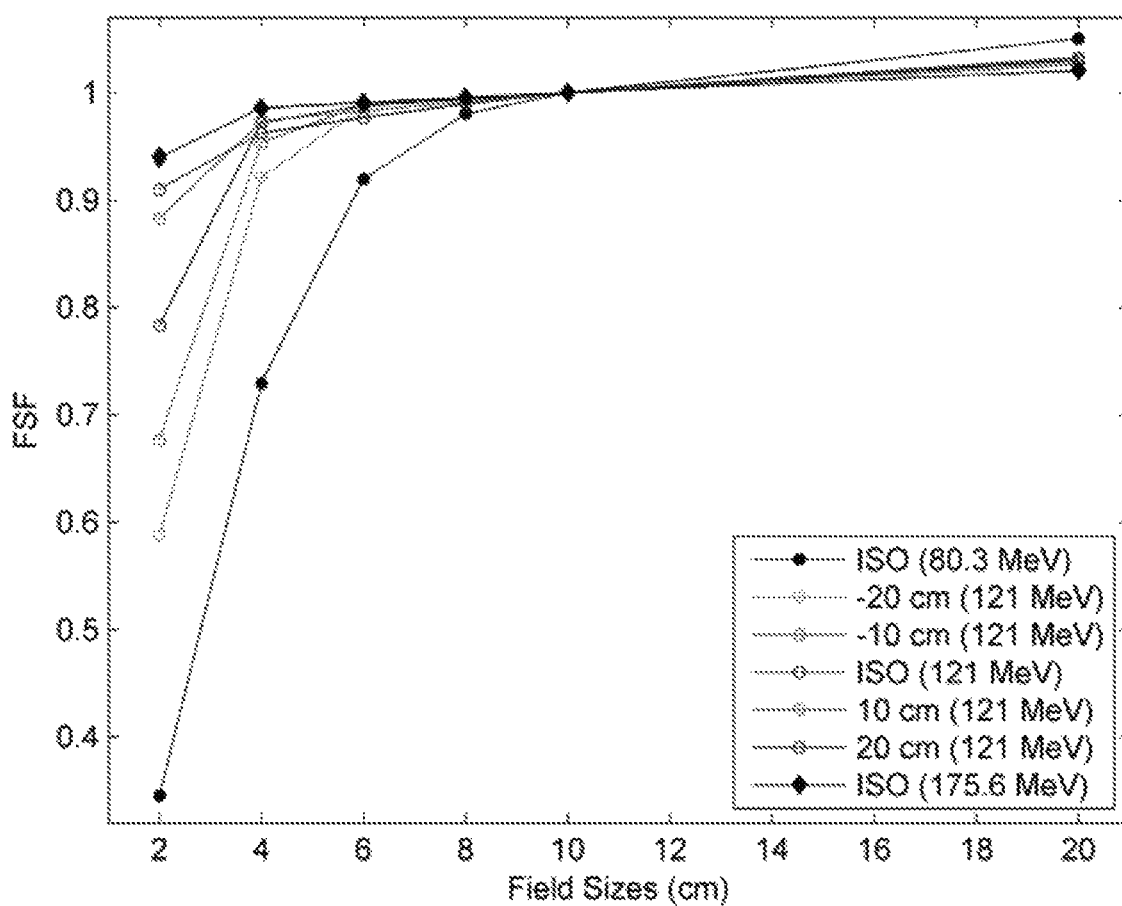
FIG. 3 shows FSFs measured in an example study at five different positions (isocenter, ±10 cm and ±20 cm) for the proton energy of 121 MeV, and at the isocenter plane for the proton energies of 80.3 Mev and 175.6 MeV.

The FSFs were obtained by normalizing the charges recorded at various field sizes to that of the 10 cm field. A total of 250 FSFs were measured and used to configure the proton fluence model. The FSFs for all five positions for 121 MeV protons are shown in FIG. 3, along with those for 80.3 MeV and 175.6 MeV protons at the isocenter position.

FSFs are relative quantities. The absolute doses in the TPS such as the Eclipse TPS can be from an integrated depth dose ("IDD"). In the commissioning process for the example study mentioned above, IDDs were generated by Monte Carlo simulation and normalized to the dose measured at a depth of 1 cm with a Bragg peak chamber. Various beams with different range values, spread-out Bragg peak ("SOBP") widths, and field sizes were generated in the Eclipse TPS. These beams were delivered to a phantom using the proton beam delivery system, and the measured doses were compared with those from the Eclipse TPS. A small adjustment (up to 2%) to the IDD dose normalization was applied in order to achieve 2% dose agreement between the measured dose and the dose calculated by Eclipse TPS.

In this example study, dose planes for patient-specific QA were measured with the DigiPhant device (IBA Dosimetry, Schwarzenbruck, Germany) at multiple depths. Measurements were also made with Gafchromic film with the one-dose protocol (Ashland, Bridgewater, N.J., USA) in order to take advantage of the high spatial resolution afforded by film measurements.

The FSF measurements described in the present disclosure utilized a spiral delivery pattern with added control points. As shown in FIG. 2, this method is very efficient because several FSFs can be obtained by delivering a single beam. For instance, in one example implementation, it took approximately three hours to measure 250 FSFs for ten energies at five different phantom positions relative to the proton nozzle. Optimal fit parameters for the proton fluence can be interpolated to other beam energies. With these efficient FSF measurements, an entire proton fluence model can be configured using direct measurements, without using any Monte Carlo simulation data. Instead, the FSF measurements provide useful information on proton fluence that can improve the Monte Carlo simulation.

While the proton fluence for a single proton spot can be measured by high resolution detectors such as film, diodes, pinpoint chambers, and scintillators, these measurements are usually time consuming, sensitive to setup errors, or need post-processing. It is especially challenging to measure the low-dose tails directly because a large number of monitor units are needed to increase the low-dose signals to the measurable level. Conversely, the FSFs can be measured using homogeneous square fields, which are less affected by setup errors. Therefore, the FSF measurements made using the methods described in the present disclosure are more accurate and robust in characterizing the proton fluence.

Because IMPT has the capability to provide high dose conformity, it has increasingly been used in treating complex tumors, such as head-and-neck cancers. For a highly-modulated plan, there are no homogenous dose distributions for any of the constituting fields, and the heavy modulation of each field generates high dose gradients inside the target. In cases such as this, it is important to have an accurate model of both the primary proton fluence and that of the extended tails. The methods described in the present disclosure allow for achieving an accurate dose calculation for an IMPT plan by providing accurate modeling of every spot, including first and second Gaussian as well as their relative weights.

It is worth noting that in some instances the proton spot profiles may not be intrinsically double-Gaussian in shape, particularly for the laterally-extending low-dose tails. In some instances, different or additional functions can be used for modeling. As one example, adding an additional Cauchy-Lorentz function may fit measured profiles better. In example studies implementing the methods described in the present disclosure, the accuracy of the fluence model was better than 2% for FSFs measured in air and in water, and for the absolute doses of the SOBP beams. These high-accuracy validations enable a precise model for the prediction of patient dose, which can result in high gamma passing rate (e.g., greater than 99%) for patient-specific QA.

In some instances, in-air proton fluence measurements for beam energies above a certain threshold may not be optimal for configuring the TPS. For instance, with increasing energy there are more nuclear interactions that produce low-dose tails (halo) in water, and some TPS systems and algorithms may have deficiencies in modeling these halos. Also, higher energy protons have larger ranges in water; thus, these protons undergo more scattering and the spot profiles change more as the beam travels through the water. Thus, in some instances the spot profiles can be measured in water and an in-air fluence model can be altered to match the in-water profiles for higher energies. As one example, in-water FSFs can be used for proton energies higher than 175.6 MeV to configure the proton fluence in the TPS. By adding the artificial proton fluence, the above-mentioned two deficiencies can be mitigated.

Figure 4:
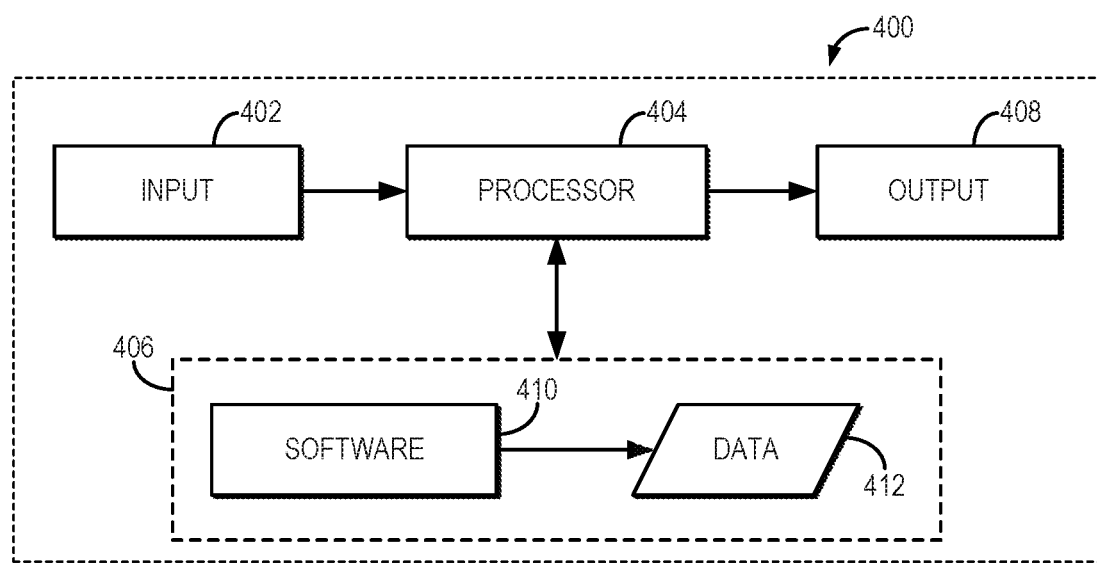
FIG. 4 is a block diagram of an example computer system that can implement the methods described in the present disclosure.

Referring now to FIG. 4, a block diagram of an example of a computer system 400 that can implement the methods described in the present disclosure is shown. The computer system 400 generally includes an input 402, at least one hardware processor 404, a memory 406, and an output 408. Thus, the computer system 400 is generally implemented with a hardware processor 404 and a memory 406.

In some embodiments, the computer system 400 can be a workstation, a notebook computer, a tablet device, a mobile device, a multimedia device, a network server, a mainframe, one or more controllers, one or more microcontrollers, or any other general-purpose or application-specific computing device. The computer system 400 can form a part of a hadron therapy system, such as a proton beam therapy system.

The computer system 400 may operate autonomously or semi-autonomously, or may read executable software instructions from the memory 406 or a computer-readable medium (e.g., a hard drive, a CD-ROM, flash memory), or may receive instructions via the input 402 from a user, or any another source logically connected to a computer or device, such as another networked computer or server. Thus, in some embodiments, the computer system 400 can also include any suitable device for reading computer-readable storage media.

In general, the computer system 400 is programmed or otherwise configured to implement the methods and algorithms described in the present disclosure. For instance, the computer system 400 can be programmed to generate control instructions for a proton therapy system, provide those control instructions to the proton therapy system to control operation of the proton beam delivery, receive radiation measurements, compute field size factors based on the radiation measurements, and quantify the output of the proton therapy system based in part on the field size factors. In some instances, the computer system 400 can be programmed to commission the proton therapy system using the field size factors. In some other instances, the computer system 400 can be programmed to perform quality assurance of the proton therapy system using the field size factors.

The input 402 may take any suitable shape or form, as desired, for operation of the computer system 400, including the ability for selecting, entering, or otherwise specifying parameters consistent with performing tasks, processing data, or operating the computer system 400. In some aspects, the input 402 may be configured to receive data, such as data acquired with a dosimeter or other radiation detector, which may be an ionization chamber. Such data may be processed as described above to compute field size factors for a number of prescribed field sizes and beam energies. In addition, the input 402 may also be configured to receive any other data or information considered useful for quantifying the output of the proton therapy system using the methods described above.

Among the processing tasks for operating the computer system 400, the one or more hardware processors 404 may also be configured to carry out any number of post-processing steps on data received by way of the input 402.

The memory 406 may contain software 410 and data 412, such as data acquired with a dosimeter or other radiation detector, and may be configured for storage and retrieval of processed information, instructions, and data to be processed by the one or more hardware processors 404. In some aspects, the software 410 may contain instructions directed to generating spot delivery patterns and control instructions for a proton therapy system, and for computing field size factors for use in commissioning the proton therapy system or performing quality assurance on the proton therapy system.

In addition, the output 408 may take any shape or form, as desired, and may be configured for displaying images and data plots, in addition to other desired information.

Figure 5A:
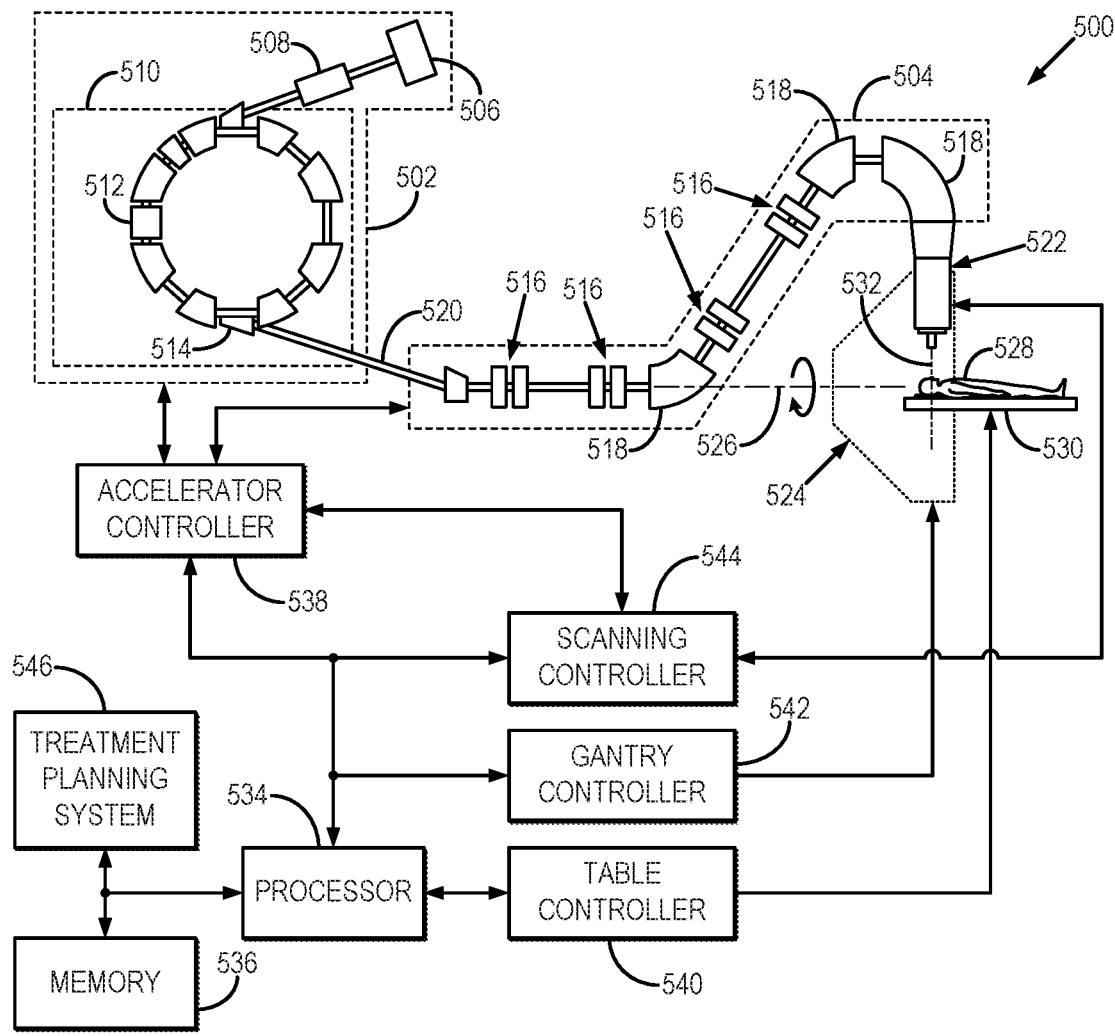
FIGS. 5A and 5B illustrate an example hadron therapy system, such as a proton therapy system, that can implement the methods described in the present disclosure.
Figure 5B:
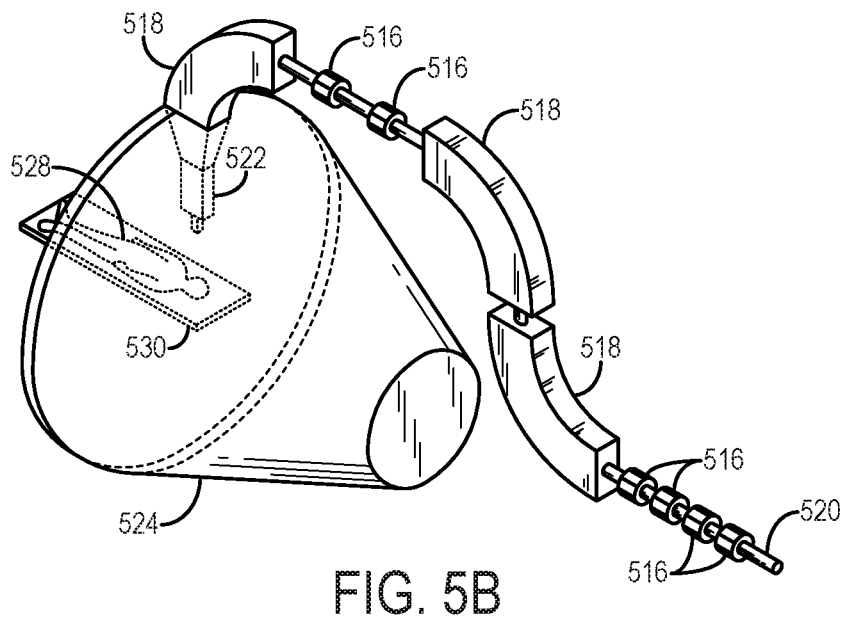

Referring now to FIGS. 5A and 5B, an example of a hadron therapy system 500, which may be a proton beam therapy system, is illustrated. Examples of hadrons for use with a hadron therapy system include protons, neutrons, and atoms or molecules containing such particles. For example, hadron therapy may include proton therapy, heavy ion therapy, and neutron therapy. An example hadron therapy system 500 generally includes a charged particle generating system 502 and a beam transport system 504. By way of example, the charged particle generating system 502 may include a synchrotron; however, in other configurations the charged particle generating system 502 may include a cyclotron. For some neutron therapy systems, the charged particle generating system 502 may include a linear accelerator ("linac") configured to operate as a deuterium-tritium ("D-T") neutron generator.

The charged particle generating unit 502 includes an ion source 506; an injector 508, such as a linac; and an accelerator 510, such as a synchrotron. The accelerator 510 includes at least one radio frequency ("RF") acceleration cavity 512. As an example, the RF acceleration cavities may include an RF applying electrode that is disposed on the circulating orbit of the accelerator 510 and an RF power source that is in electrical communication with the RF applying electrode by way of a switch.

Ions generated in the ion source 506, such as hydrogen ions (i.e., protons) or carbon ions, are accelerated by the injector 508 to form an ion beam that is injected into the accelerator 510. The accelerator 510 provides energy to the injected ion beam by way of the acceleration cavity 512, where RF energy is applied to the ion beam. In the case of a synchrotron, quadrupole and dipole magnets are used to steer the ion beam about the accelerator 510 a number of times so that the ion beam repeatedly passes through the acceleration cavity 512. After the energy of the ion beam traveling in the accelerator 510 has reached a preselected, desired energy level (e.g., 100-200 MeV), the ion beam is extracted from the accelerator 510 through an extraction deflector 514. Extraction may occur by way of bumping, or kicking, the ion beam to an outer trajectory so that it passes through a septum, or by way of resonance extraction.

The beam transport system 504 includes a plurality of focusing magnets 516 and steering magnets 518. Examples of focusing magnets 516 include quadrupole magnets, and examples of steering magnets 518 include dipole magnets. The focusing magnets 516 and steering magnets 518 are used to contain the ion beam in an evacuated beam transport tube 520 and to deliver the ion beam to a beam delivery device 522 that is situated in a treatment room.

The beam delivery device 522 is coupled to a rotatable gantry 524 so that the beam delivery device 522 may be rotated about an axis of rotation 526 to delivery therapeutic radiation to a patient 528 positioned on a patient table 530. The rotatable gantry 524 supports the beam delivery device 522 and deflection optics, including focusing magnets 516 and steering magnets 518, that form a part of the beam transport system 504. These deflection optics rotate about the rotation axis 526 along with the beam delivery device 522. Rotation of the rotatable gantry 524 may be provided, for example, by a motor (not shown in FIGS. 5A and 5B).

In some configurations, the accelerator 510 provides an ion beam to a plurality of beam delivery devices located in different treatment rooms. In such configurations, the beam transport system 504 may connect to a series of switchyards that may include an array of dipole bending magnets that deflect the ion beam to any one of a plurality of deflection optics that each lead to a respective beam delivery device in the respective treatment room.

The beam delivery device 522 is designed to deliver precise dose distributions to a target volume within a patient. In general, an example beam delivery device 522 includes components that may either modify or monitor specific properties of an ion beam in accordance with a treatment plan. The beam delivery device 522 may, for example, include a device to spread or otherwise modify the ion beam position and profile, a dispersive element to modify the ion beam energy, and a plurality of beam sensors to monitor such properties. For example, scanning electromagnets may be used to scan the ion beam in orthogonal directions in a plane that is perpendicular to a beam axis 532. As another example, the beam delivery device 522 can include a range shifter ("RS"). For instance, in the example study described above, a fixed range shifter with a water equivalent thickness ("WET") of 4.5 cm was attached at the end of the nozzle of the beam delivery device 522, 30 cm from isocenter.

The hadron therapy system 500 is controlled by a central controller that includes a processor 534 and a memory 536 in communication with the processor 534. An accelerator controller 538 is in communication with the processor 534 and is configured to control operational parameters of the charged particle generating system 502, including the accelerator 510 and the beam transport system 504. A table controller 540 is in communication with the processor 534 and is configured to control the position of the patient table 530. A gantry controller 542 is also in communication with the processor 534 and is configured to control the rotation of the rotatable gantry 524. A scanning controller 544 is also in communication with the processor and is configured to control the beam delivery device 522. The memory 536 may store a treatment plan prescribed by a treatment planning system 546 that is in communication with the processor 534 and the memory 536, in addition to control parameters or instructions to be delivered to the accelerator controller 538, the table controller 540, the gantry controller 542, and the scanning controller 544. The memory 536 may also store relevant patient information that may be utilized during a treatment session.

Before the ion beam is provided to the patient 528, the patient 528 is positioned so that the beam axis 532 intersects a treatment volume in accordance with a treatment plan prescribed by a treatment planning system 546. The patient 528 is positioned by way of moving the patient table 530 into the appropriate position. The patient table 530 position is controlled by the table controller 540, which receives instructions from the processor 534 to control the position of the patient table 530. The rotatable gantry 524 is then rotated to a position dictated by the treatment plan so that the ion beam will be provided to the appropriate treatment location in the patient 528. The rotatable gantry 524 is controlled by the gantry controller 542, which receives instructions from the processor 534 to rotate the rotatable gantry 524 to the appropriate position. As indicated above, the position of the ion beam within a plane perpendicular to the beam axis 532 may be changed by the beam delivery device 522. The beam delivery device 522 is instructed to change this scan position of the ion beam by the scanning controller 544, which receives instruction from the processor 534. For example, the scanning controller 544 may control scanning electromagnets located in the beam delivery device 522 to change the scan position of the ion beam.

The present disclosure has described one or more preferred embodiments, and it should be appreciated that many equivalents, alternatives, variations, and modifications, aside from those expressly stated, are possible and within the scope of the invention.

The invention claimed is:

1. A method for quantifying an output of a proton therapy system, the steps of the method comprising:
   (a) generating control instructions for a proton therapy system with a computer system, the control instructions defining a spot delivery pattern through which a proton beam is to be moved, the spot delivery pattern comprising:
      a plurality of spot delivery pattern segments each corresponding to different field sizes;
      a plurality of control points, each control point separating a first and second spot delivery pattern segment selected from the plurality of spot delivery pattern segments and defining a proton beam pause time during which the proton beam is paused;
      wherein the plurality of spot delivery pattern segments collectively define a spiral pattern that begins at a center of a field-of-view of the proton therapy system and spirals outward to a periphery of the field-of-view;
   (b) providing the control instructions to the proton therapy system;
   (c) operating the proton therapy system using the control instructions, wherein a radiation measurement is acquired by a radiation detector during each proton beam pause time, each radiation measurement being associated with one of the different field sizes;
   (d) computing with the computer system, a plurality of field size factors including a field size factor for each of the different field sizes using the radiation measurements acquired for that different field size; and
   (e) quantifying an output of the proton therapy system based in part on the plurality of field size factors.

2. The method as recited in claim 1, wherein the spot delivery pattern defines a pencil beam scanning pattern.

3. The method as recited in claim 1, wherein step (c) includes operating the proton therapy system for a plurality of different beam energies using the control instructions, thereby acquiring radiation measurements for each of the different field sizes at each of the different beam energies.

4. The method as recited in claim 1, wherein the radiation detector comprises an ionization chamber.

5. The method as recited in claim 4, wherein the radiation measurement includes an in-air proton fluence measurement.

6. The method as recited in claim 4, wherein the radiation measurement includes an in-water proton fluence measurement.

7. The method as recited in claim 1, wherein computing the field size factors includes normalizing the field size factors based on a radiation measurement acquired in a selected field size.

8. The method as recited in claim 1, wherein the plurality of spot delivery pattern segments are spatially contiguous.

9. The method as recited in claim 1, wherein step (e) comprises configuring a dose computation model for a treatment planning system using the plurality of field size factors.

10. The method as recited in claim 9, wherein the dose computation model is a double-Gaussian dose model.

11. The method as recited in claim 1, wherein step (e) comprises performing quality assurance of the proton therapy system based on the plurality of field size factors.

12. A method for controlling the operation of a proton therapy system, the steps of the method comprising:
(a) extracting a proton beam from a synchrotron;
(b) transporting the proton beam from the synchrotron through a nozzle to a radiation detector; and
(c) scanning the proton beam over the radiation detector along a spot delivery pattern comprising:
a plurality of spot delivery pattern segments each corresponding to different field sizes;
a plurality of control points, each control point separating a first and second spot delivery pattern segment selected from the plurality of spot delivery pattern segments and defining a proton beam pause time during which delivery of the proton beam is paused;
wherein the plurality of spot delivery pattern segments collectively define a spiral pattern that begins at a center of a field-of-view of the proton therapy system and spirals outward to a periphery of the field-of-view.

13. The method as recited in claim 12, wherein the spot delivery pattern defines a pencil beam scanning pattern.

14. The method as recited in claim 12, wherein step (c) includes operating the proton therapy system for a plurality of different beam energies.

15. The method as recited in claim 12, wherein the plurality of spot delivery pattern segments are spatially contiguous.

16. A controller for controlling the operation of a proton therapy system, comprising:
a memory having stored thereon instructions defining a spot delivery pattern comprising:
a plurality of spot delivery pattern segments each corresponding to different field sizes;
a plurality of control points, each control point separating a first and second spot delivery pattern segment selected from the plurality of spot delivery pattern segments and defining a proton beam pause time during which a proton beam is to be paused;
wherein the plurality of spot delivery pattern segments collectively define a spiral pattern that begins at a center of a field-of-view and spirals outward to a periphery of the field-of-view;
a processor in communication with the memory and operable to receive the instructions stored on the memory that when implemented on the processor cause the processor to control the operation of a proton therapy system to deliver a proton beam along the spot delivery pattern and to measure radiation during each proton beam pause time.

17. The controller as recited in claim 16, wherein the processor is programmed to operate the proton therapy system for a plurality of different beam energies using the instructions, thereby acquiring radiation measurements for each of the different field sizes at each of the different beam energies.

18. The controller as recited in claim 16, wherein the processor is programmed to compute a field size factor for each of the different field sizes based on radiation measurements acquired for that different field size.

19. The controller as recited in claim 18, wherein the processor is programmed to compute each field size factor by normalizing the field size factors based on a radiation measurement acquired in a selected field size.

* * * * *